United States Patent [19]

Arena

[11] Patent Number: 4,581,447

[45] Date of Patent: Apr. 8, 1986

[54] PROCESS FOR MAKING A MIXTURE OF L-GLUCOSE AND L-MANNOSE

[75] Inventor: Blaise J. Arena, Des Plaines, Ill.

[73] Assignee: UOP Inc., Des Plaines, Ill.

[21] Appl. No.: 640,472

[22] Filed: Aug. 13, 1984

[51] Int. Cl.$^4$ .............................................. C07H 1/00
[52] U.S. Cl. .................................... 536/125; 536/124
[58] Field of Search ........................ 536/1.1, 124, 125

[56] References Cited

U.S. PATENT DOCUMENTS

| | | | |
|---|---|---|---|
| 2,584,129 | 2/1952 | Hockett | 536/124 |
| 3,850,905 | 11/1974 | Tumerman et al. | 536/125 |
| 4,207,413 | 6/1980 | Szarek et al. | 536/1 |
| 4,262,032 | 4/1981 | Levin | 426/658 |
| 4,371,616 | 2/1983 | Hulbers | 435/105 |
| 4,421,568 | 12/1983 | Hulbers | 127/48 |
| 4,440,855 | 4/1984 | Horwath et al. | 435/105 |

OTHER PUBLICATIONS

Speck, Jr., "Advances in Carbohydrate Chemistry", vol. 13, 1958, pp. 63–69.
M. L. Wolfrom and A. Thompson, *J. Am. Chem. Soc.*, 68, 791, (1946).

*Primary Examiner*—Johnnie R. Brown
*Attorney, Agent, or Firm*—Thomas K. McBride; William H. Page, II; Eugene I. Snyder

[57] ABSTRACT

A process converting L-arabinose to L-fructose in high yield and selectivity is described. The success of the process depends upon careful pH control during cyanohydrin formation from L-arabinose and its subsequent selective hydrogenation, the choice of hydrogenation conditions, including catalyst, temperature, and pressure, to selectively convert the cyano group to the imine group with subsequent hydrolysis to the aldehyde group without any significant hydrogenation of the latter, and upon the use of performing reactions, including base catalyzed isomerization, in an atmosphere of an inert gas.

5 Claims, 1 Drawing Figure

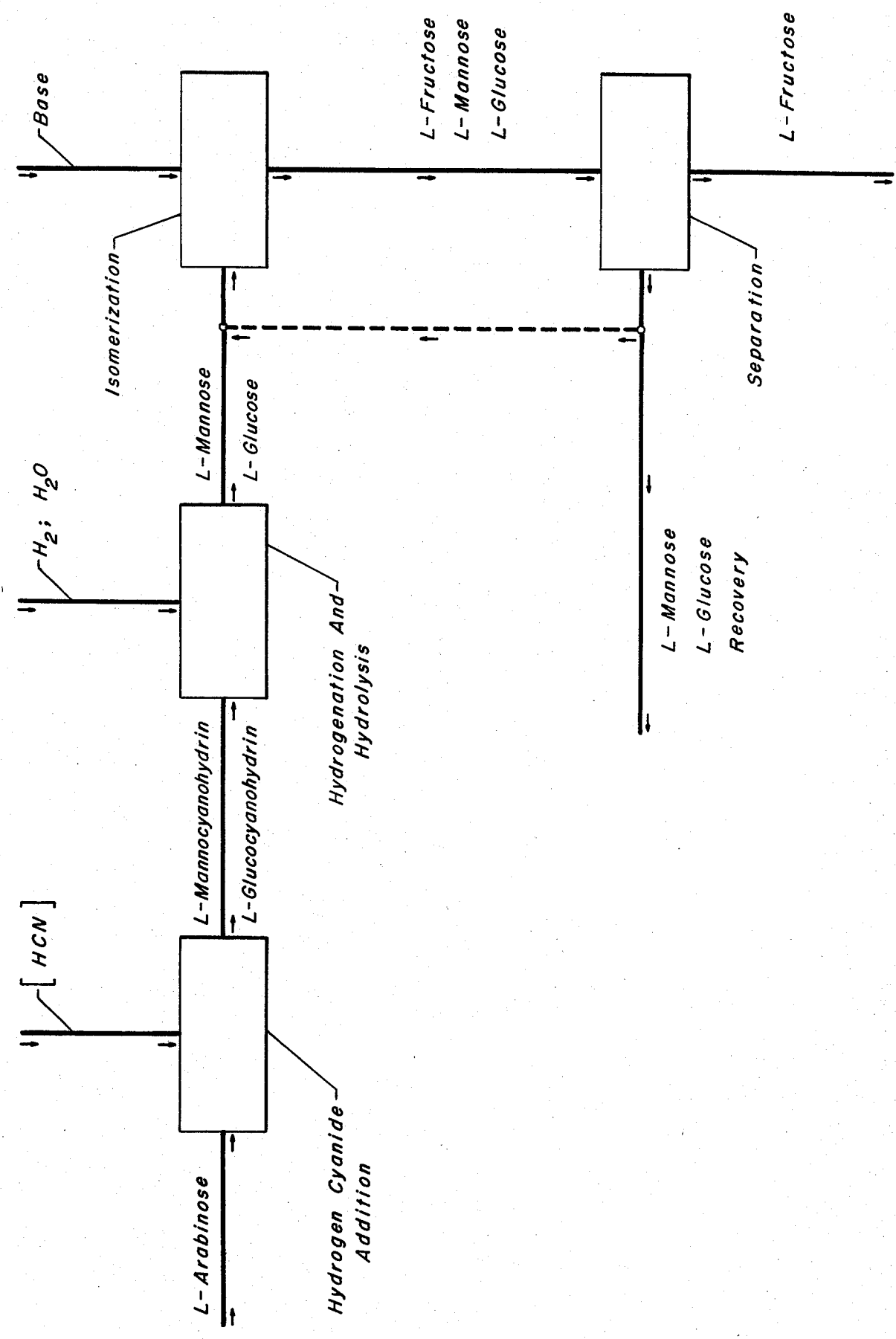

4,581,447

PROCESS FOR MAKING A MIXTURE OF L-GLUCOSE AND L-MANNOSE

BACKGROUND OF THE INVENTION

Present dietetic needs, predilections, and perceptions have led to the increased use of artificial sweeteners as a replacement for the "natural" sugars, including sucrose and fructose. Such artificial sweeteners are highly imperfect, including being under continual review for their long term physiological affects, yet their demand has grown unabated. Accompanying their growth as a commercial area with substantial economic impact has been a renewed emphasis on discovering and supplying new artificial sweeteners.

The ideal artificial sweetener would be noncaloric, noncariogenic, without detrimental physiological effects, and usable by diabetics. All these requirements would be met if a sweetener were not metabolized by humans and by flora which are found in the mouth and intestinal tract, and if the sweetener were either not absorbed by humans, or absorbed without effect on any internal organ. That is, the ideal sweetener should be excreted in the same form as when ingested. Another desirable feature is that it have bulk properties similar to sucrose so that it can be substituted for table sugar in many formulations. Recently, and perhaps belatedly, attention has turned toward the L-sugars as desirable artificial sweeteners. It has been known since at least 1946 that L-fructose is sweet (M. L. Wolfrom and A. Thompson, *J. Am. Chem. Soc.*, 68, 791,793 (1946)), and since at least 1890 that L-fructose is nonfermentable (E. Fischer, *Ber. Deutsch. Chem. Ges.*, 23, 370,389 (1890)), hence not metabolized by microorganisms generally metabolizing D-sugars. Given that L-fructose is a sweet nonmetabolite it becomes obvious to use it as a noncaloric sweetener in many formulations.

Exploitation of the favorable properties of L-sugars is hindered by their relative unavailability. L-fructose, for example, is not found to any significant extent in nature. This unavailability has spurred recent efforts in developing commercially feasible methods for preparing L-sugars in amounts necessary for their use as a staple of commerce. U.S. Pat. Nos. 4,371,616 and 4,421,568 describe a method of producing L-sugars, including L-idose and L-glucose, from the readily available D-glucose. Although the preparation of a number of L-sugars is described in U.S. Pat. No. 4,262,032 the focus seems to be on typical laboratory methods wholly unsuited for economical industrial production, in contrast to the process herein. U.S. Pat. No. 4,440,855 uses glucose oxidase to convert L-glucose to L-glucosone. To the extent that there are suitable procedures adaptable to the large scale production of L-glucose as well as the conversion of L-glucosone to L-fructose, the teachings of the patentee relate to the preparation of L-fructose. The subject matter of U.S. Pat. No. 4,207,413 is L-sucrose, the enantiomer of ordinary table sugar, which can be hydrolyzed to afford L-fructose.

None of the art cited above fulfills the need for an economically and commercially feasible process for the preparation of L-fructose. Such a process requires, inter alia, a readily accessible starting material, preferably one with the L-configuration. L-arabinose, obtained from the hydrolysis of lignocellulosics, is one of few naturally occurring L-sugars and is abundant. The subject matter of this application is the conversion of L-arabinose to L-fructose. Since the products of this invention include L-glucose and L-mannose as well, it is clear that the process which is this invention relates to their preparation as well as that of L-fructose. Because L-fructose currently is the L-sugar of greatest interest the following material speaks primarily to its preparation, nonetheless it is to be understood that the processes described and claimed are directed toward L-glucose and L-mannose equally well.

SUMMARY OF THE INVENTION

In one aspect the invention herein is a method of converting L-arabinose to a mixture of L-glucose and L-mannose. In another aspect the invention herein is a method of making L-fructose from L-arabinose.

DESCRIPTION OF THE FIGURE

FIG. 1 is a flow diagram for the process of this invention.

DESCRIPTION OF THE INVENTION

The processes described herein are conveniently summarized according to the following equations.

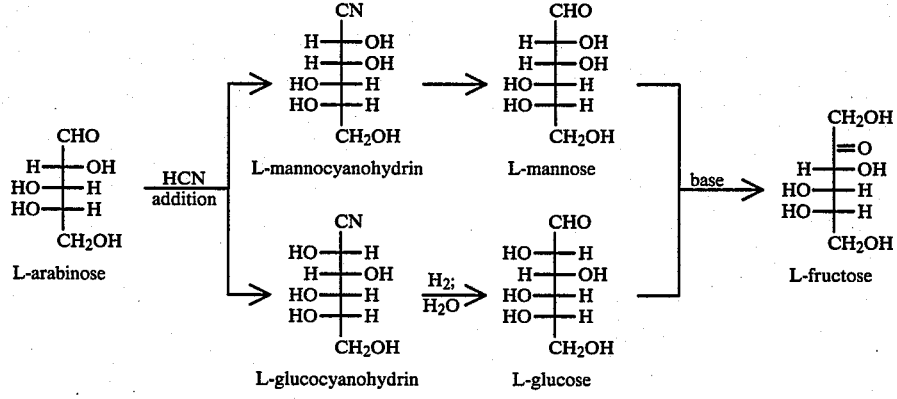

The gross features of each of the above reactions are previously known. For example, see J. C. Sowden, *Methods in Carbohydrate Chemistry*, V. I, page 132 (1962) for HCN addition; A. S. Serianni, *Can. J. Chem.*, 57, 3160 (1979) for hydrogenation-hydrolysis; E. R. Garrett, *J. Org. Chem.*, 35, 3502 (1970) for isomerization. However this invention incorporates a substantial improvement in each step. Additionally, the invention herein combines the operations so as to obviate the necessity of isolating any intermediate. The result is the conversion of a feedstock of L-arabinose to L-fructose using the described sequence of steps in an economically and industrially attractive manner conservative of time, cost, and materials. This result is not possible in light of the prior art, but is made possible only by the disclosures elaborated upon within.

The first step in the process which is my invention is the conversion of L-arabinose to a mixture of L-glucocyanohydrin and L-mannocyanohydrin by the reaction of a cyanide source with L-arabinose. Suitable cyanide sources include cyanide salts, such as those of alkali metals, with sodium and potassium cyanide being favored, as well as other water soluble salts furnishing cyanide ion, and hydrocyanic acid or hydrogen cyanide. An essential feature of my invention is that during the course of the reaction the pH is maintained between about 7.0 and about 9.0, most preferably between about 7.8 and 8.2. In the absence of this pH control additional products are formed which reduce the yield of the cyanohydrins, which interfere in subsequent reactions of the process, and which complicate the isolation of L-fructose. Control of pH can be conveniently effected by the addition of a weak, water soluble acid, especially carboxylic acids such as formic acid, acetic acid, propionic acid, butyric acid, valeric acid, and so on.

During the reaction the temperature is maintained between about 10° and about 40° C., desirably between about 15° and 30° C., and most desirably between 20° and 25° C. An aqueous solution of arabinose may be added to the cyanide source, or the cyanide source may be added to an aqueous solution of arabinose. The former method is somewhat preferred but is not considered particularly critical. It has been found that a cyanide-arabinose ratio of two affords optimum results, with no advantage being offered by a relatively larger proportion of cyanide. It is highly desirable to conduct the addition in an inert atmosphere. By an inert atmosphere is meant a gas which does not react with either of the reactants or any of the products formed in the reaction. Examples of suitable inert gases include nitrogen, helium, hydrogen, argon, krypton, xenon, neon, and so forth. The reaction time is inverse to reaction temperature. At about 22° C. for a 3.3 molar solution of arabinose reaction time is about 1 hour.

After the reaction of L-arabinose is complete, the solution containing the cyanohydrin mixture is acidified to a pH between about 1.0 and about 5.0, more preferably between about 1.5 and 2.5 while maintaining the temperature at no more than about 25° C. Temperature control is necessary to avoid product decomposition, and acidification is performed in an inert atmosphere. Any nonpoisoning acid with respect to the hydrogenation catalyst used in the subsequent step may be used, with sulfuric acid being a particularly convenient acid.

The next step is the selective hydrogenation of the cyanohydrins to their corresponding imines with subsequent hydrolysis of the imines to their corresponding aldehydes under conditions where the resulting aldehydes are not hydrogenated. Therefore, the catalyst used in this hydrogenation is selective both in the context of converting the nitrile group only to the imine,

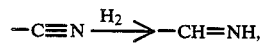

and being selective in having essentially no catalytic activity toward reduction of the aldehyde group. I have found that a catalyst of supported zerovalent palladium performs these functions especially effectively. Among the supports which may be used barium sulfate and titania, and especially the former, are particularly preferred, although other supports such as silicas, aluminas, magnesia, various clays, and so on may be used, but not necessarily with equivalent results. The catalyst is used in an amount sufficient to furnish from about 0.5% to about 5% palladium, based on the L-arabinose originally used, with the particular amount chosen depending upon the desired reaction time. An amount sufficient to furnish from about 1% to about 3% by weight palladium is convenient.

The hydrogenation pressure and temperature chosen results from a delicate interplay of selectivity and reaction time. Increasing the pressure and temperature decreases both selectivity and reaction time. A range giving acceptable selectivity without requiring inordinately long reaction times includes a hydrogen pressure from about atmospheric to about 80 psig and a temperature from about 10° to about 50° C. Hydrogen pressures between about 30 and about 50 psig are especially preferred, and a temperature between about 20° and about 40° C. is particularly desirable.

It has been found that the selectivity of hydrogenation, both in the context of reduction of the cyano group to imine, subsequent hydrolysis of the imine to the aldehyde, and nonhydrogenation of the resulting aldehyde, is a function of pH. Consequently, it is desired that the initial pH be between about 1.0 and about 5.0. In a variant of the process claimed the pH is maintained between about 1.0 and 5.0 throughout the hydrogenation. A pH range between about 1.5 and 2.5, especially 1.7 and 2.3, is particularly preferred. Under such conditions a reaction time between about 12 and 24 hours at 30° C. using 40 psig hydrogen and an amount of a catalyst affording 2.5% palladium leads to complete disappearance of cyanohydrin. The composition of the resulting hydrogenation mixture is about a 60:40 mixture of L-mannose:L-glucose in a total yield up to about 85% based on L-arabinose.

The resulting mixture of L-glucose and L-mannose is isomerized in a basic medium to L-fructose, preferably in the presence of a fructose-complexing agent. By complexing fructose the agent tends to shift the equilibrium toward the fructose side, thereby increasing the amount of fructose which may be formed in the isomerization. Among fructose complexing materials which may be used are included aluminates, such as sodium and potassium aluminates, borates such as sodium and potassium borate, phenyl borate, aluminate exchanged resin, and various germanates. The complexing agent may be used in an amount up to about 1 molar proportion based upon the amount of L-arabinose used initially.

Isomerization is conducted at a pH between about 8.5 and about 12.5, especially between about 9.5 and about 11.5. The desired pH may be obtained by the addition of base to the mixture resulting from hydrogenation, or by ion exchange treatment of the hydrogenation mixture followed by addition of base. The latter approach is operationally preferable so as to reduce the total volume and salt content during isomerization.

Isomerization is conducted in an inert atmosphere at a temperature between about 20° and about 50° C., especially between about 30° and about 40° C. Reaction times of about 48 hours are common under these conditions to afford fructose in about a 40% yield from the glucose-mannose mixture. The remainder of the glucose and mannose is largely unchanged under the preceding reaction conditions, i.e., few if any by-products are formed according to my process.

Following isomerization the L-fructose is recovered by suitable means, for example, the isomerization mixture may be subjected to ion exchange to remove all or most of the dissolved salts. From the resulting solution, which is largely a mixture of L-fructose, L-glucose, and L-mannose, the fructose may be recovered by suitable separation methods, such as by membrane separation, chromatographic adsorption, and so on. An exemplary method is described in U.S. Pat. Nos. 4,014,711, 4,157,267, 4,340,724, and 4,402,832.

The example which follows is merely illustrative of the process of this invention which is not to be limited thereto.

EXAMPLE

The large size reactor system used in this process was an 8-liter vessel equipped with stirring means, an internal cooling and heating coil, pH and temperature monitors, and various ports for reactant addition and product removal. The vessel also could be purged with nitrogen, evacuated, or pressurized with hydrogen as required.

Cyanide addition. A solution of 639.7 g of sodium cyanide in 2500 ml of distilled water at pH 11.53 was added to the vessel and the head space above the solution was purged with nitrogen for 10 minutes. The solution was cooled to 7° C. and concentrated acetic acid was slowly added until the pH was 7.94. The temperature was allowed to rise to 16° C., after which 1,666 g of a 60 wt. % aqueous solution of L-arabinose was added. The reaction was allowed to proceed at 23° C. while the pH was maintained at 8.0±0.1 with dropwise addition of acetic acid. After 1.25 hours 385 ml of concentrated sulfuric acid was added with cooling to bring the pH to 2.05. The unreacted hydrogen cyanide was removed by evacuating the vessel to 30 inches mercury with stirring at 20° C. Analysis of this product showed approximately 100% L-arabinose conversion.

Hydrogenation and hydrolysis. To the cyanide addition product under a blanket of nitrogen was added 500 g of 5% palladium on barium sulfate. The reactor was pressured to 40 psig with hydrogen and brought to 35° C. The pH of the hydrogenation-hydrolysis reactions was maintained at about 2.0 by occasional addition of concentrated sulfuric acid. When hydrogen consumption ceased the product was removed and filtered to separate the catalyst and the solution was ion exchanged to remove the bulk of the dissolved salts. Analysis of this product showed approximately 100% conversion of the intermediate cyanohydrins, with a 75% yield of glucose and mannose in a ratio of about 2:3.

Isomerization. A solution (20 ml) containing 5.8 wt. % glucose and 10.9% mannose was adjusted to pH 10.8 with concentrated sodium hydroxide. To this was added 1.6 g of sodium aluminate giving an approximately 1:1 molar ratio of aluminate to total sugars. The mixture was heated at 37° C. for 48 hours under nitrogen and was analyzed by high-pressure liquid chromatography. The product contained 26.8% L-fructose based on the dissolved solids, which represents a 35.2% theoretical yield. The L-fructose thus prepared was separated and recovered by chromatography.

What is claimed is:

1. A process for converting L-arabinose to a mixture of L-glucose and L-mannose comprising reacting L-arabinose with a source of cyanide at a temperature between about 10° and about 40° C., in an atmosphere of an inert gas, where the pH is maintained between about 7.0 and about 9.0 during the reaction, to afford a mixture containing the cyanohydrins of L-glucose and L-mannose, acidifying the solution of cyanohydrins with a nonpoisoning acid to a pH between about 1.0 and about 5.0 at a temperature no greater than about 25° C. in an atmosphere of an inert gas, hydrogenating the resulting solution using an effective amount of supported zerovalent palladium as a catalyst at a hydrogen Pressure no greater than about 80 psig, at a temperature between about 10° C. and about 50° C., and maintaining the pH between about 1.5 and about 2.5, and recovering the resulting mixture containing L-glucose and L-mannose.

2. The process of claim 1 where the temperature is maintained between about 15° and about 30° C. during the reaction between L-arabinose and the cyanide source.

3. The process of claim 2 where the temperature is between about 20° and about 25° C.

4. The process of claim 1 where the hydrogenation catalyst support is barium sulfate.

5. The process of claim 1 where the hydrogenation temperature is between about 20° and about 40° C.

* * * * *